(12) United States Patent
Bennett

(10) Patent No.: US 6,242,652 B1
(45) Date of Patent: Jun. 5, 2001

(54) PROCESS FOR PRODUCING ORGANIC TRISULFIDES

(75) Inventor: Brooks D. Bennett, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/518,124

(22) Filed: Mar. 3, 2000

(51) Int. Cl.[7] ............... C07C 321/12; C07C 321/22; C07C 321/24
(52) U.S. Cl. ................................. 568/26; 568/21
(58) Field of Search ......................... 568/21, 26

(56) References Cited

U.S. PATENT DOCUMENTS

| | | | |
|---|---|---|---|
| 3,308,166 | * 3/1967 | Biensan et al. . | |
| 3,392,201 | * 7/1968 | Warner . | |
| 5,155,275 | 10/1992 | Shaw | 568/21 |
| 5,232,623 | 8/1993 | Shaw | 252/183.13 |
| 5,442,123 | 8/1995 | Arretz et al. | 568/26 |
| 5,530,163 | 6/1996 | Shaw | 568/26 |
| 5,861,539 | * 1/1999 | Shaw | 568/26 |
| 5,907,064 | * 5/1999 | Shaw | 568/21 |
| 6,051,739 | * 4/2000 | Shaw | 568/26 |

OTHER PUBLICATIONS

CA:124:8235 abs of US5442123, Aug. 1995.*
CA:713172 abs of Z Naturforsch B by Steudel et al 24(3) pp 351–2, 1969.*

* cited by examiner

*Primary Examiner*—Jean F. Vollano
(74) *Attorney, Agent, or Firm*—Kameron D. Kelly; Charles W. Stewart

(57) ABSTRACT

Selectively producing organic trisulfides by contacting, in the presence of a catalyst, a mercaptan and a sulfur compound under conditions sufficient to produce a organic polysulfides and hydrogen sulfide and controlling the concentration of hydrogen sulfide in the liquid reaction solution during specific reaction periods such that the production of organic trisulfide is enhanced and the production organic polysulfides having more or less than three sulfur atoms is inhibited.

48 Claims, No Drawings

PROCESS FOR PRODUCING ORGANIC TRISULFIDES

The present invention relates to a process for selectively producing organic trisulfides.

BACKGROUND OF THE INVENTION

Organic polysulfides, especially organic trisulfides, are useful for many purposes such as additives for elastomers, antioxidants for lubricating oils, intermediates for the production of organic chemicals, insecticides, and germicides, and additives for diesel fuels to improve cetane number and ignition qualities. Organic polysulfides are also useful in the compounding of high pressure lubricants and in the acceleration of rubber treating processes.

Organic polysulfides can be produced by reacting mercaptans with elemental sulfur in the presence of a catalyst. The reaction can generally be depicted as follows:

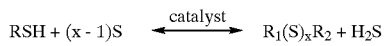

$$RSH + (x-1)S \xrightarrow{\text{catalyst}} R_1(S)_x R_2 + H_2S$$

where R, $R_1$ and $R_2$ are alkyl radicals, generally containing 1 to 20 carbon atoms, which can be the same or different, x is an integer from 2 to 10, and x is the average number of sulfur atoms per polysulfide molecule in the product.

The product of the above reaction typically comprises a distribution of individual organic polysulfide compositions, each containing a different number of sulfur atoms. In many commercial applications, especially for use in high pressure lubricants, organic trisulfides exhibit more desirable properties than other organic polysulfides. For example, organic polysulfides containing more than three sulfur atoms exhibit high copper-strip corrosivity (ASTM Copper Strip Corrosion Test D-130-56), rendering them unsatisfactory for many commercial applications. In addition, organic disulfides can be undesirable because they have a high flash point and exhibit poor lubrication properties.

If an organic polysulfide product contains a high quantity of organic polysulfides having more or less than three sulfur atoms, costly separation processes and equipment are necessary to remove undesirable polysulfides and recover a more pure organic trisulfide product that is suitable for commercial purposes. Therefore, a reaction product having a distribution of organic polysulfides which maximizes the amount of organic trisulfides while minimizing the amount of other organic polysulfides is desired.

Several processes exist for the preparation of high purity organic trisulfides; however, most existing processes require materials, conditions, and/or steps which make commercial implementation uneconomical. For example, the trisulfide selective process taught in U.S. Pat. No. 5,442,123 requires expensive process equipment, an expensive catalyst, and low reaction temperatures, which increase the required reaction time. Thus, it is desirable to develop a process for selectively producing organic trisulfides which minimizes equipment, labor, and time and employs a relatively inexpensive catalyst.

SUMMARY OF THE INVENTION

An object of the present invention is to provide a process for selectively producing organic trisulfides.

Another object of the inventive process is to provide a reaction product having a higher concentration of organic trisulfides than products from conventional processes for making organic polysulfides.

A further object of the inventive process is to provide a reaction product having a lower concentration of organic disulfides than products from conventional processes for making organic polysulfides.

A still further object of the inventive process is to provide a reaction product having a lower concentration of organic polysulfides containing more than three sulfur atoms than products from conventional processes for making organic polysulfides.

An even further object of the present invention is to eliminate the need for expensive processes and equipment necessary to separate organic trisulfides from other organic polysulfides.

A still further object of the inventive process is to eliminate costly materials, conditions, and/or steps which are required by conventional methods of selectively producing organic trisulfides.

Other objects and advantages of the present invention will become more apparent as the invention is more fully disclosed hereinbelow.

According to an embodiment of the present invention, a process for the selective production of organic trisulfides is provided. The process comprises contacting, in a reaction vessel, a mercaptan, a sulfur compound, and a catalyst under reaction conditions sufficient to produce an organic polysulfide product and hydrogen sulfide. During the reaction, the concentration of hydrogen sulfide in the liquid phase within the reaction vessel is increased to a desired concentration. After the desired hydrogen sulfide concentration is reached, the hydrogen sulfide produced by the reaction is trapped in the reaction vessel until the organic polysulfide product within the reaction vessel has a desired distribution of organic polysulfides.

DETAILED DESCRIPTION OF THE INVENTION

It has been discovered that the weight ratio of organic trisulfides to organic disulfides in a reaction product produced by reacting a mercaptan and a sulfur compound in the presence of a catalyst can be increased by controlling the concentration of hydrogen sulfide in the liquid reaction solution during specific reaction time periods.

As used herein, the term "liquid reaction solution" means a mixture of liquid phase compounds present in a reaction vessel. The composition of the liquid reaction solution of the present invention changes as the reaction progresses, but during at least a portion of the reaction period the liquid reaction solution can comprise unreacted mercaptan, unreacted sulfur compound, the catalyst, organic polysulfides, and hydrogen sulfide.

The mercaptan suitable for use as a reactant in the process of the present invention can be any mercaptan having the formula of RSH, wherein R is a hydrocarbyl radical having 1 to about 30, preferably about 1 to about 20, and most preferably 2 to 15 carbon atoms. The hydrocarbyl radical can be linear or branched and can be alkyl, aryl, cycloalkyl, alkylaryl, aralkyl, alkenyl radicals, or combinations of two or more thereof. Preferably the hydrocarbyl radical is an alkyl radical. Presently preferred mercaptans are tertiary mercaptans. The presently most preferred mercaptan is t-butyl mercaptan.

The sulfur compound suitable for use as a reactant in the process of the present invention can be any sulfur containing compound capable of reacting with a mercaptan to produce an organic trisulfide and hydrogen sulfide. Preferably the sulfur compound is elemental sulfur.

The amount of sulfur compound contacted with the mercaptan depends on the desired sulfur content of the organic polysulfide product. For an average sulfur content of q sulfurs per polysulfide molecule, (q-1) moles of sulfur must be added per 2 moles of mercaptan and 1 mole of hydrogen sulfide will be produced per 2 moles of mercaptans reacted. It is, however, preferred that about 0.5 to about 10, preferably about 1.0 to about 5, and most preferably 1.0 to 2.0 moles of mercaptan per mole of sulfur is used.

The catalyst suitable for use in the process of the present invention can be any catalyst capable of catalyzing the reaction of a mercaptan and a sulfur compound to form hydrogen sulfide and an organic trisulfide. The presently preferred catalyst comprises a basic catalyst which can be an inorganic base, an organic base, or combinations of two or more thereof. Suitable organic bases include, but are not limited to tetramethylammonium hydroxide, tetraethylammonium hydroxide, tetrapropylammonium hydroxide, tetramethylammonium bisulfide, tetraethylammonium bisulfide, trimethylamine, triethylamine, n-butylamine and combinations of two or more thereof. Suitable inorganic bases include, but are not limited to, lithium hydroxide, sodium hydroxide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R_1ONa$, $R_1SNa$, and combinations of any two or more thereof; where $R_1$ is a $C_1$–$C_{18}$ alkyl radical, or combinations of any two or more thereof. Presently, the amine catalysts are not as preferred as other catalysts, and an inorganic base is preferred because of the availability and low cost of inorganic bases. Among the inorganic bases, sodium hydroxide is preferred because it is readily available and inexpensive.

The catalyst useful in the process of the present invention can further comprise an alkoxylated compound, preferably and alkoxylated alcohol. The alkoxylated alcohol useful in the present invention has a general formula of $R_2O[CH_2CH(R_3)O]_mH$ where $R_2$ is a $C_1$–$C_{20}$ hydrocarbyl radical selected from the group consisting of alkyl radical, alkylaryl radical, aryl radical, cycloalkyl radical and alkenyl radical. Preferably $R_2$ is a $C_6$–$C_{18}$ alkyl radical. Most preferably $R_2$ is a $C_{10}$–$C_{16}$ alkyl radical. Preferably $R_3$ is selected from the group consisting of hydrogen, $C_1$–$C_{16}$ alkyl radicals, and $C_2$–$C_{16}$ alkenyl radicals. Preferably $R_3$ is a hydrogen or a $C_1$–$C_3$ alkyl radical. Most preferably $R_3$ is hydrogen. Preferably m is a number from 1 to about 20, more preferably from about 2 to about 12, and most preferably from 5 to 10. An example of a suitable alkoxylated alcohol is TERGITOL® 15-S-7 which is an ethoxylated alcohol, manufactured and marketed by Union Carbide Corporation, and having the formula of $R_2O(CH_2CH_2O)_7H$ where $R_2$ is a secondary alkyl radical having 11–15 carbon atoms and 7 is the average number of the ethylene oxide units. Another example is an ethoxylated phenol having the same number of ethylene oxide units. Other suitable alkoxylated alcohols are also available from Union Carbide Corporation.

The weight ratio of base to alkoxylated compound in the catalyst can vary widely so long as the ratio can catalyze the reaction of a mercaptan and a sulfur compound. Preferably the weight ratio of a base to an alkoxylated compound is from about 10:1 to about 1:100, more preferably from about 2:1 to about 1:10, most preferably from 1:1 to 1:5.

The amount of catalyst contacted with the mercaptan and sulfur compound of the present invention is any amount that can catalyze the formation of an organic polysulfide. The weight of the catalyst as a percentage of the weight of mercaptans can be in the range of from about 0.001 to about 10 percent, preferably from about 0.01 to about 3 percent, and most preferably from 0.05 to 2 percent.

The organic polysulfides produced by the reaction of a mercaptan and a sulfur compound can be any organic polysulfides having the formula of $RS_xR$, wherein each R can be the same or different and are each a hydrocarbyl radical having 1 to about 30, preferably 1 to about 20, and most preferably 2 to about 15 carbon atoms and x is a number from 2 to about 10, preferably 2 to 6, more preferably 3 to 5, and most preferably 3. The hydrocarbyl radical can be linear or branched and can be alkyl, aryl, cycloalkyl, alkylaryl, aralkyl, alkenyl radicals, or combinations of two or more thereof. Preferably the hydrocarbyl radical is an alkyl radical. Preferred organic polysulfides are di-t-butyl polysulfides. The most preferred organic polysulfide is di-t-butyl trisulfide.

The process of the present invention is commenced by contacting the mercaptan, the sulfur compound, and the catalyst in a reaction vessel. The contacting is generally accomplished by slowly adding one of the reactants to a mixture of the other reactant and the catalyst. The contacting of the reactants and the catalyst can take place in any suitable reaction vessel.

The reaction of the mercaptan and sulfur compound can commence at ambient conditions, but it is generally desirable to accelerate the reaction by stirring and/or increasing the temperature of the liquid reaction solution. It is preferred in practicing the process of the present invention for a high reaction temperature to be employed in order to allow for shorter reaction times. The reaction temperature can be from about 30° C. to about 250° C., preferably from about 50° C. to about 150° C., more preferably from about 80° C. to about 130° C., and most preferably from 95° C. to 115° C. The reaction pressure can vary widely from about 1 atmosphere to about 20 atmospheres, preferably from about 1 atmosphere to about 10 atmospheres.

When the mercaptan and sulfur compound react, hydrogen sulfide evolves. The evolved hygrogen sulfide is generally present within the reaction vessel in both the liquid phase, as part of the liquid reaction solution, and in the gas phase. Typically, hydrogen sulfide evolves much more rapidly during the initial portion of the mercaptan/sulfur reaction than during the final portion of the mercaptan/sulfur reaction. In order to prevent undesirably high pressures within the reaction vessel, it is typically required for the gaseous hydrogen sulfide to be vented from the reaction vessel for a "hydrogen sulfide venting period".

An important aspect of the present invention is for the total amount of hydrogen sulfide vented from the reaction vessel during the hydrogen sulfide venting period to be less than the total amount of hydrogen sulfide evolved from the mercaptan/sulfur reaction during the hydrogen sulfide venting period, thereby providing a concentration of hydrogen sulfide in the liquid reaction solution which increases during the hydrogen sulfide venting period.

In accordance with the present invention, the hydrogen sulfide venting period commences with the commencement of the mercaptan/sulfur reaction and terminates when the amount of hydrogen sulfide in the liquid reaction solution reaches a "desired hydrogen sulfide concentration". The desired hydrogen sulfide concentration is such that the weight of hydrogen sulfide as a percentage of the total weight of the liquid reaction solution is from about 0.1 percent to about 10 percent, preferably from about 0.3 to about 5 percent, more preferably from about 0.5 to about 2 percent, and most preferably from 0.8 percent to 1.5 percent.

Although the desired hydrogen sulfide concentration can be reached rapidly by employing a very slow rate of hydrogen sulfide venting, it is preferred in practicing the present invention for the rate of hydrogen sulfide venting to be such that the hydrogen sulfide venting period is sufficiently long to allow the majority of the sulfur compound employed as a reactant to be converted into other compound. Preferably, the hydrogen sulfide venting period is such that at least about 50 weight percent, more preferably at least about 75 weight percent, and most preferably at least 90 weight percent of the sulfur compound is converted into other compounds.

During the hydrogen sulfide venting period the amount of hydrogen sulfide and sulfur compound present in the liquid reaction solution can be measured by any means known in the art, for example, by gas chromatograph.

The hydrogen sulfide venting period can typically be from about 0.2 hours to about 20 hours, preferably from about 0.5 hours to about 8 hours, and most preferably from 1 hour to 3 hours.

An essential aspect of the present invention is for the release of hydrogen sulfide from the reaction vessel to be terminated when the amount of hydrogen sulfide in the liquid reaction solution reaches the desired hydrogen sulfide concentration. Thus, after the hydrogen sulfide venting period, the hydrogen sulfide within the reaction vessel is trapped in the reaction vessel for a "hydrogen sulfide trapping period".

The trapping of hydrogen sulfide within the reaction vessel is accomplished by any method known in the art that can prevent the release of hydrogen sulfide from a reaction vessel. Generally, the trapping of hydrogen sulfide within the reaction vessel is accomplished by sealing all the contents of the reaction vessel within the reaction vessel. Thus, during the hydrogen sulfide trapping period, the means for venting hydrogen sulfide from the reaction vessel should be blocked in order to prevent the release of hydrogen sulfide from the reaction vessel.

The hydrogen sulfide trapping period commences at the end of the hydrogen sulfide venting period and terminates when the organic polysulfide product has a desired organic polysulfide distribution. A desired organic polysulfide distribution preferably has a weight percent of organic trisulfides that is greater than about 75 percent, more preferable greater than about 85 percent, even more preferable greater than about 90 percent, and most preferable greater than 92 percent of the total weight of the organic polysulfide product. A desired organic polysulfide distribution preferably has a weight ratio of organic trisulfides to organic disulfides which is greater than about 25:1, preferably greater than about 50:1, more preferably greater than about 65:1, and most preferably greater than 75:1. A desired organic polysulfide product preferably has a weight ratio of organic trisulfides to organic tetrasulfides which is greater than about 5:1, preferably greater than about 15:1, more preferably greater than about 20:1, and most preferably greater than about 25:1.

To determine when the liquid reaction solution contains an organic polysulfide product of desired organic polysulfide distribution, the composition of the liquid reaction product can be monitored during the hydrogen sulfide trapping period. The composition of the liquid reaction solution can be monitored by any method known in the art, for example, by sampling and gas chromatograph analysis.

The hydrogen sulfide trapping period can typically be from about 0.1 hours to about 10 hours, preferably from about 0.2 hours to about 5 hours, and most preferably from 0.5 hour to 2 hours.

After the hydrogen sulfide trapping period, the liquid reaction solution can be contacted with carbon dioxide to provide a stable organic polysulfide product. As used herein, the term "stable" refers to an organic polysulfide product that does not substantially turn cloudy or hazy or increase mercaptan content during the production or storage for at least 30 days, preferably 6 months. The term "substantially" means more than trivial.

The amount of carbon dioxide required to produce a stable organic polysulfide product can be in the range of from about 0.1 to about 100,000, preferably about 0.5 to about 10,000, and most preferably 1 to 1,000 molar equivalent of the base used in the catalyst. The contacting of the liquid reaction solution with carbon dioxide can be carried out under any conditions that are effective to produce a stable organic polysulfide product or can reduce susceptibility of the organic polysulfide product to decomposition during heating or sparging.

The residual hydrogen sulfide present in the liquid reaction solution after the hydrogen sulfide trapping period can be removed by venting. Removal of the residual hydrogen sulfide can take place before or after contacting the liquid reaction solution with carbon dioxide to produce a stable organic polysulfide product.

After residual hydrogen sulfide has been removed and the liquid reaction solution has been stabilized, the unreacted mercaptan can be removed by any means known to one skilled in the art such as, for example, distillation and nitrogen sparging.

Further purification, separation, and recovery methods known to one skilled in the art can be used to recover a substantially pure organic polysulfide product.

The process of the present invention provides an organic polysulfide product of superior organic polysulfide distribution by ensuring that a sufficient amount of hydrogen sulfide is present in the liquid reaction solution to enhance the formation of organic trisulfides while inhibiting the formation of organic polysulfides having more or less than three sulfur atoms.

The following examples are provided to further illustrate the practice of the present invention and are not intended to limit the scope of the invention of the claims.

EXAMPLE I

The following example demonstrates a conventional method of preparing polysulfides by reacting a mercaptan and a sulfur in the presence of a basic catalyst.

A 100 gallon Hastelloy C reactor (R-100) was initially charged with 135 pounds of flour sulfur, 200 gm of 50% sodium hydroxide, and 200 gm of ethoxylated alcohol (Union Carbide TERGITOL® 15-S-7). A 200 gallon Hastelloy C vessel (R-200) was charged with 585 pounds of t-butyl mercaptan. The mercaptan was transferred to R-100 by pressurizing R-200 to 200 psig with nitrogen and opening a control valve located in the line connecting the two reactors. When all the mercaptan was transferred from R-200 to R-100 the control valve was closed. The transfer of mercaptan from R-200 to R-100 resulted in a pressure in R-100 of about 160 psig.

The agitator in R-100 was turned on, and the contents of R-100 were stirred for 10 minutes. The R-100 overhead vent valve was opened slowly to reduce the pressure in R-100 to less than 5 psig. While the agitator was running, the contents of R-100 were heated to a temperature of 80° C. over a period of 20 minutes and held at that temperature for 10 minutes. While R-100 was heated to and maintained at 80° C., gaseous hydrogen sulfide was released through a restrictive orifice valve. The temperature in R-100 was then increased to and maintained at about 105° C. for a 3 hour reaction period during which gaseous hydrogen sulfide was released through the restrictive orifice valve.

After the 3 hour reaction period the contents of R-100 were cooled to less than 45° C. and R-100 was vented to 0 psig. The contents of R-100 were then contacted with carbon dioxide to neutralize the basic catalyst. This caustic neutralization step was performed by pressurizing R-100 to 50 psia with carbon dioxide and turning on the roll pump in R-100 for 4 hours. After the roll pump was turned off, the contents of R-100 were cooled to 35° C. and R-100 was vented to less than 5 psig.

The bulk of the t-butyl mercaptan (TBM) was recovered by vacuum distillation. Residual TBM was then removed by nitrogen sparging leaving a di-t-butyl polysulfide product. The disulfides and tetrasulfides were then separated from the trisulfides by vacuum distillation.

Table 1 shows the distribution of di, tri, and tetrasulfides in the di-t-butyl polysulfide product for four runs employing the conventional process of this example.

TABLE 1

| Run | di-t-Butyl Disulfide (wt. %) | di-t-Butyl Trisulfide (wt. %) | Di-t-Butyl Tetrasulfide (wt. %) |
| --- | --- | --- | --- |
| 1 | 3.24 | 84.9 | 11.9 |
| 2 | 5.18 | 88.3 | 6.5 |
| 3 | 3.02 | 90.96 | 5.66 |
| 4 | 3.48 | 92.86 | 3.37 |
| Average | 3.73 | 89.25 | 6.86 |

EXAMPLE II

The following example demonstrates the inventive method of preparing polysulfides by reacting a mercaptan and sulfur in the presence of a basic catalyst.

The inventive process was carried out using the same process employed in Example 1, except, during the 3 hour reaction period when R-100 was heated to about 105° C., the venting of gaseous hydrogen sulfide through the restrictive orifice valve was stopped when the amount of hydrogen sulfide in the liquid phase in the reaction vessel was between about 0.5 and 2 weight percent by weight of the entire liquid phase in the reaction vessel. Throughout the remainder of the 3 hour reaction period the reaction vessel was sealed and the hydrogen sulfide remained trapped in the reaction vessel.

Table 2 shows the distribution of di, tri, and tetrasulfides in the di-t-butyl polysulfide product for seven runs employing the inventive process of this example.

TABLE 2

| Run | di-t-Butyl Disulfide (wt. %) | di-t-Butyl Trisulfide (wt. %) | Di-t-Butyl Tetrasulfide (wt. %) |
| --- | --- | --- | --- |
| 1 | 1.84 | 91.9 | 6.3 |
| 2 | 0.78 | 94.2 | 5.0 |
| 3 | 1.06 | 92.31 | 6.14 |
| 4 | 0.65 | 92.66 | 6.00 |
| 5 | 1.11 | 94.85 | 3.76 |
| 6 | 1.34 | 90.94 | 7.72 |
| 7 | 1.75 | 93.64 | 4.61 |
| Average | 1.22 | 92.93 | 5.65 |

Table 2 shows that the inventive process is more selective towards di-t-butyl trisulfide than the conventional process. The inventive process increased trisulfide production by an average of 3.7 weight percent and decreased the amount of disulfide in the polysulfide product to about one-third that of the conventional process. The average weight ratio of trisulfide to disulfide increased from about 25:1 for the conventional process to about 75:1 for the inventive process.

The specific examples herein disclosed are to be considered as being primarily illustrative. Various changes beyond those described will no doubt occur to those skilled in the art, and such changes are to be understood as forming a part of this invention insofar as they fall within the spirit and scope of the appended claims.

That which is claimed is:

1. A process for selectively producing organic trisulfides, said process comprises the steps of:
    (a) contacting a mercaptan, a sulfur compound, and a catalyst in a reaction vessel under reaction conditions sufficient to produce a reaction product comprising an organic polysulfide product and hydrogen sulfide, thereby creating within said reaction vessel a liquid reaction solution comprising a mixture of liquid phase compounds in said reaction vessel, wherein a hydrogen sulfide concentration is present in said liquid reaction solution;
    (b) when said hydrogen sulfide concentration reaches a desired hydrogen sulfide concentration, trapping the hydrogen sulfide in said reaction vessel for a hydrogen sulfide trapping period which extends until said organic polysulfide product has a desired distribution of organic polysulfides, wherein said desired hydrogen sulfide concentration is such that the weight of hydrogen sulfide as a percentage of the total weight of said liquid reaction solution is from about 0.1 percent to about 10 percent, and wherein said desired distribution of organic polysulfides is such that said organic polysulfide product has (1) a weight percent of organic trisulfides that is greater than about 75 percent of the total weight of said organic polysulfide product, (2) a weight ratio of organic trisulfides to organic disulfides that is greater than about 25:1, and (3) a weight ratio of organic trisulfides to organic tetrasulfides that is greater than about 5:1; and
    (c) thereafter, recovering said organic polysulfide product.

2. A process according to claim 1 wherein said desired hydrogen sulfide concentration is such that the weight of hydrogen sulfide as a percentage of the total weight of said liquid reaction solution is from about 0.3 percent to about 5 percent.

3. A process according to claim 1 wherein said desired hydrogen sulfide concentration is such that the weight of hydrogen sulfide as a percentage of the total weight of said liquid reaction solution is from about 0.5 percent to about 2 percent.

4. A process according to claim 1 wherein said catalyst comprises an inorganic base.

5. A process according to claim 1 wherein said catalyst comprises sodium hydroxide.

6. A process according to claim 1 wherein said hydrogen sulfide trapping period is from about 0.2 hours to about 20 hours.

7. A process according to claim 1 wherein said hydrogen sulfide trapping period is from about 0.1 hours to about 10 hours.

8. A process according to claim 1 further comprising the step of, after step (b) and before step (c), contacting said liquid reaction solution with carbon dioxide, thereby stabilizing said organic polysulfide product.

9. A process according to claim 1 wherein said desired distribution of organic polysulfides is such that said organic polysulfide product has (1) a weight percent of organic trisulfides that is greater than about 85 percent of the total weight of said organic polysulfide product, (2) a weight ratio of organic trisulfides to organic disulfides that is greater than about 50:1, and (3) a weight ratio of organic trisulfides to organic tetrasulfides that is greater than about 15:1.

10. A process according to claim 9 wherein said desired hydrogen sulfide concentration is such that the weight of hydrogen sulfide as a percentage of the total weight of said liquid reaction solution is from about 0.3 percent to about 5 percent.

11. A process according to claim 10 wherein said catalyst comprises an inorganic base.

12. A process according to claim 11 wherein said hydrogen sulfide trapping period is from about 0.1 hours to about 10 hours.

13. A process according to claim 1 wherein said desired distribution of organic polysulfides is such that said organic polysulfide product has (1) a weight percent of organic trisulfides that is greater than about 90 percent of the total weight of said organic polysulfide product, (2) a weight ratio of organic trisulfides to organic disulfides that is greater than about 65:1, and (3) a weight ratio of organic trisulfides to organic tetrasulfides that is greater than about 20:1.

14. A process according to claim 13 wherein said desired hydrogen sulfide concentration is such that the weight of hydrogen sulfide as a percentage of the total weight of said liquid reaction solution is from about 0.5 percent to about 2 percent.

15. A process according to claim 14 wherein said catalyst comprises sodium hydroxide.

16. A process according to claim 15 wherein said hydrogen sulfide trapping period is from about 0.2 hours to about 5 hours.

17. A process according to claim 16 wherein said mercaptan is t-butyl mercaptan and said sulfur compound is elemental sulfur.

18. A process according to claim 17 further comprising the step of, after step (b) and before step (c), contacting said liquid reaction solution with carbon dioxide, thereby stabilizing said organic polysulfide product.

19. A process for selectively producing organic trisulfides, said process comprises the steps of:
(a) contacting a mercaptan, a sulfur compound, and a catalyst in a reaction vessel under reaction conditions sufficient to a produce reaction product comprising an organic polysulfide product and hydrogen sulfide, thereby creating within said reaction vessel a liquid reaction solution comprising a mixture of liquid phase compounds in said reaction vessel, wherein a hydrogen sulfide concentration is present in said liquid reaction solution;
(b) venting gaseous hydrogen sulfide from said reaction vessel for a hydrogen sulfide venting period which extends until said hydrogen sulfide concentration reaches a desired hydrogen sulfide concentration, wherein said desired hydrogen sulfide concentration is such that the weight of hydrogen sulfide as a percentage of the total weight of said liquid reaction solution is from about 0. percent to about 10 percent;
(c) thereafter, trapping the hydrogen sulfide in said reaction vessel for a hydrogen sulfide trapping period which extends until said organic polysulfide product has a desired distribution of organic polysulfides, wherein said desired distribution of organic polysulfides is such that said organic polysulfide product has (1) a weight percent of organic trisulfides that is greater than about 75 percent of the total weight of said organic polysulfide product, (2) a weight ratio of organic trisulfides to organic disulfides that is greater than about 25:1, and (3) a weight ratio of organic trisulfides to organic tetrasulfides that is greater than about 5:1; and
(d) thereafter, recovering said organic polysulfide product.

20. A process according to claim 19 further comprising the step of, after step (c) and before step (d), contacting said liquid reaction solution with carbon dioxide, thereby stabilizing said organic polysulfide product.

21. A process according to claim 19 wherein said desired distribution of organic polysulfides is such that said organic polysulfide product has (1) a weight percent of organic trisulfides that is greater than about 85 percent of the total weight of said organic polysulfide product, (2) a weight ratio of organic trisulfides to organic disulfides that is greater than about 50:1, and (3) a weight ratio of organic trisulfides to organic tetrasulfides that is greater than about 15:1.

22. A process according to claim 21 wherein said desired hydrogen sulfide concentration is such that the weight of hydrogen sulfide as a percentage of the total weight of said liquid reaction solution is from about 0.3 percent to about 5 percent.

23. A process according to claim 22 wherein said catalyst comprises an inorganic base.

24. A process according to claim 23 wherein said hydrogen sulfide venting period is from about 0.2 hours to about 20 hours.

25. A process according to claim 24 wherein said hydrogen sulfide trapping period is from about 0.1 hours to about 10 hours.

26. A process according to claim 19 wherein said desired distribution of organic polysulfides is such that said organic polysulfide product has (1) a weight percent of organic trisulfides that is greater than about 90 percent of the total weight of said organic polysulfide product, (2) a weight ratio of organic trisulfides to organic disulfides that is greater than about 65:1, and (3) a weight ratio of organic trisulfides to organic tetrasulfides that is greater than about 20:1.

27. A process according to claim 26 wherein said desired hydrogen sulfide concentration is such that the weight of hydrogen sulfide as a percentage of the total weight of said liquid reaction solution is from about 0.5 percent to about 2 percent.

28. A process according to claim 27 wherein said catalyst comprises sodium hydroxide.

29. A process according to claim 28 wherein said hydrogen sulfide venting period is from about 0.5 hours to about 8 hours.

30. A process according to claim 29 wherein said hydrogen sulfide trapping period is from about 0.2 hours to about 5 hours.

31. A process according to claim 30 wherein said mercaptan is t-butyl mercaptan and said sulfur compound is elemental sulfur.

32. A process according to claim 31 further comprising the step of, after step (c) and before step (d), contacting said liquid reaction solution with carbon dioxide, thereby stabilizing said organic polysulfide product.

33. A process for selectively producing organic trisulfides, said process comprises the steps of:
   (a) contacting a mercaptan, elemental sulfur, and a catalyst in a reaction vessel under reaction conditions sufficient to produce a reaction product comprising an organic polysulfide product and hydrogen sulfide, thereby creating within said reaction vessel a liquid reaction solution comprising a mixture of liquid phase compounds in said reaction vessel, wherein a hydrogen sulfide concentration is present in said liquid reaction solution, and wherein an elemental sulfur concentration is present in said liquid reaction solution;
   (b) venting gaseous hydrogen sulfide from said reaction vessel for a hydrogen sulfide venting period, wherein gaseous hydrogen sulfide is vented in an amount such that said hydrogen sulfide concentration is increased during said hydrogen sulfide venting period;
   (c) simultaneously with step (b), measuring said hydrogen sulfide concentration to obtain a measured hydrogen sulfide concentration;
   (d) simultaneously with step (b), measuring said elemental sulfur concentration to obtain a measured elemental sulfur concentration;
   (e) when said measured hydrogen sulfide concentration equals a desired hydrogen sulfide concentration and when said measured elemental sulfur concentration equals a desired elemental sulfur concentration, trapping the hydrogen sulfide in said reaction vessel for a hydrogen sulfide trapping period, wherein said desired hydrogen sulfide concentration is such that the weight of hydrogen sulfide as a percentage of the total weight of said liquid reaction solution is from about 0.1 percent to about 10 percent, and wherein said desired elemental sulfur concentration is such that the weight of elemental sulfur in said liquid reaction solution is less than 50 percent of the total weight of elemental sulfur employed as a reactant;
   (f) simultaneously with step (c), measuring the distribution of organic polysulfides in said organic polysulfide product to obtain a measured distribution of organic polysulfides; and
   (g) when said measured distribution of organic polysulfides is equal to a desired distribution of organic polysulfides, recovering said organic polysulfide product, wherein said desired distribution of organic polysulfides is such that said organic polysulfide product has (1) a weight percent of organic trisulfides that is greater than about 75 percent of the total weight of said organic polysulfide product, (2) a weight ratio of organic trisulfides to organic disulfides that is greater than about 25:1, and (3) a weight ratio of organic trisulfides to organic tetrasulfides that is greater than about 5:1.

34. A process according to claim 33 further comprising the step of, after step (e) and before step (g), contacting said liquid reaction solution with carbon dioxide, thereby stabilizing said organic polysulfide product.

35. A process according to claim 33 wherein said desired distribution of organic polysulfides is such that said organic polysulfide product has (1) a weight percent of organic trisulfides that is greater than about 85 percent of the total weight of said organic polysulfide product, (2) a weight ratio of organic trisulfides to organic disulfides that is greater than about 50:1, and (3) a weight ratio of organic trisulfides to organic tetrasulfides that is greater than about 15:1.

36. A process according to claim 35 wherein said desired elemental sulfur concentration is such that the weight of elemental sulfur in said liquid reaction solution is less than 25 percent of the total weight of elemental sulfur employed as a reactant.

37. A process according to claim 36 wherein said desired hydrogen sulfide concentration is such that the weight of hydrogen sulfide as a percentage of the total weight of said liquid reaction solution is from about 0.3 percent to about 5 percent.

38. A process according to claim 37 wherein said catalyst comprises an inorganic base.

39. A process according to claim 38 wherein said hydrogen sulfide venting period is from about 0.2 hours to about 20 hours.

40. A process according to claim 39 wherein said hydrogen sulfide trapping period is from about 0.1 hours to about 10 hours.

41. A process according to claim 33 wherein said desired distribution of organic polysulfides is such that said organic polysulfide product has (1) a weight percent of organic trisulfides that is greater than about 90 percent of the total weight of said organic polysulfide product, (2) a weight ratio of organic trisulfides to organic disulfides that is greater than about 65:1, and (3) a weight ratio of organic trisulfides to organic tetrasulfides that is greater than about 20:1.

42. A process according to claim 41 wherein said desired elemental sulfur concentration is such that the weight of elemental sulfur in said liquid reaction solution is less than 10 percent of the total weight of elemental sulfur employed as a reactant.

43. A process according to claim 42 wherein said desired hydrogen sulfide concentration is such that the weight of hydrogen sulfide as a percentage of the total weight of said liquid reaction solution is from about 0.5 percent to about 2 percent.

44. A process according to claim 43 wherein said catalyst comprises sodium hydroxide.

45. A process according to claim 44 wherein said hydrogen sulfide venting period is from about 0.5 hours to about 8 hours.

46. A process according to claim 45 wherein said hydrogen sulfide trapping period is from about 0.2 hours to about 5 hours.

47. A process according to claim 46 wherein said mercaptan is t-butyl mercaptan.

48. A process according to claim 47 further comprising the step of, after step (e) and before step (g), contacting said liquid reaction solution with carbon dioxide, thereby stabilizing said organic polysulfide product.

* * * * *